United States Patent
Kim et al.

(10) Patent No.: US 10,413,520 B2
(45) Date of Patent: Sep. 17, 2019

(54) ORAL PHARMACOLOGICAL COMPOSITION INCLUDING 5-{4-(AMINO SULFONYL)PHENYL}-2,2-DIMETHYL-4-(3-FLUOROPHENYL)-3(2H)-FURANONE HAVING CRYSTALLINE STRUCTURE WITH EXCELLENT STABILITY

(71) Applicant: CRYSTALGENOMICS, INC., Gyeonggi-do (KR)

(72) Inventors: Byung-Ha Kim, Seoul (KR); Sik Il Ahn, Gyeonggi-do (KR); Jae-Yeon Park, Seoul (KR); Tae Ryong Kim, Seoul (KR); Joong Myung Cho, Seoul (KR); Seonggu Ro, Seoul (KR)

(73) Assignee: CRYSTALGENOMICS, INC., Gyeonggi-do (KR)

( * ) Notice: Subject to any disclaimer, the term of this patent is extended or adjusted under 35 U.S.C. 154(b) by 0 days.

(21) Appl. No.: 15/630,502

(22) Filed: Jun. 22, 2017

(65) Prior Publication Data
US 2018/0008571 A1 Jan. 11, 2018

Related U.S. Application Data

(63) Continuation-in-part of application No. 15/114,181, filed as application No. PCT/KR2015/001002 on Jan. 29, 2015, now abandoned.

(30) Foreign Application Priority Data

Jan. 29, 2014 (KR) .................. 10-2014-0011315

(51) Int. Cl.
*A61K 31/341* (2006.01)
*A61K 9/48* (2006.01)
*A61K 9/20* (2006.01)

(52) U.S. Cl.
CPC .......... *A61K 31/341* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/48* (2013.01); *A61K 9/485* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| 5,536,752 A | 7/1996 | Ducharme et al. |
| 2004/0242640 A1 | 12/2004 | Desai et al. |
| 2005/0222251 A1* | 10/2005 | Park .................. A61K 31/34 514/473 |

FOREIGN PATENT DOCUMENTS

| KR | 10-0495389 | 10/2001 |
| KR | 10-2010-0096512 | 9/2010 |
| KR | 10-2013-0078147 A | 7/2013 |
| KR | 20130078147 | * 10/2013 |
| WO | 2000-0061571 | 10/2000 |
| WO | WO2000/061571 | * 10/2000 |
| WO | 2007-052937 A2 | 5/2007 |

OTHER PUBLICATIONS

KR20130078147 Machine Translation, accessed Dec. 21, 2016.*
"Manual of Pharmaceutical Science", Nanzando Co., Ltd. The 2nd edition, pp. 10-16, Mar. 31, 1998. Relevancy known to Applicant is explained in Japanese Office Action.
European Search Report and Written Opinion for co-pending Application No. 15742755.0 dated Aug. 3, 2017.
Japanese office action from corresponding Japanese Application No. 2016-549250 dated Jun. 27, 2017. (English Translation)

* cited by examiner

*Primary Examiner* — Melissa L Fisher
(74) *Attorney, Agent, or Firm* — Christensen, Fonder, Dardi & Herbert PLLC; Peter S. Dardi

(57) ABSTRACT

The present invention relates to a pharmaceutical composition including (i) as a major ingredient, a novel 5-{4-(Aminosulfonyl)phenyl}-2,2-dimethyl-4-(3-fluorophenyl)-3(2H)-furanone compound (Formula 1) or a pharmaceutically acceptable salt thereof, which has a crystalline form A or G, or a mixed form thereof and has a 50% volume particle diameter ($d_{(0.5)}$) of 3 μm to 9 μm and a 90% volume particle diameter ($d_{(0.9)}$) of 10 μm to 50 μm, (ii) a pharmaceutically acceptable diluent, and (iii) a pharmaceutically acceptable lubricant. The pharmaceutical composition of the present invention has the advantages of good stability, high dissolution rate, improved content uniformity, and excellent pharmacokinetic properties. Due to these advantages, as a non-steroidal anti-inflammatory drug, the pharmaceutical composition of the present invention may be effective in treating inflammation or pain.

9 Claims, 11 Drawing Sheets

ORAL PHARMACOLOGICAL COMPOSITION INCLUDING 5-{4-(AMINO SULFONYL)PHENYL}-2,2-DIMETHYL-4-(3-FLUOROPHENYL)-3(2H)-FURANONE HAVING CRYSTALLINE STRUCTURE WITH EXCELLENT STABILITY

CROSS REFERENCE TO RELATED APPLICATIONS

This application is a continuation-in-part of copending U.S. patent application Ser. No. 15/141,181 with a 35 U.S.C. 371(c) date of Jul. 26, 2016, which is a national stage filing of PCT application PCT/KR2015/001002 to Kim et al., filed on Jan. 29, 2015, which claims priority to Korean patent application 10-2014-0011315 filed on Jan. 29, 2014, all of which are incorporated herein by reference.

TECHNICAL FIELD

The present invention relates to an oral pharmacological composition including 5-{4-(aminosulfonyl)phenyl}-2,2-dimethyl-4-(3-fluorophenyl)-3(2H)-furanone having a crystalline structure with excellent stability. More specifically, the present invention relates to a method for preparing the 5-{4-(aminosulfonyl)phenyl}-2,2-dimethyl-4-(3-fluorophenyl)-3(2H)-furanone having a crystalline structure with enhanced stability, and a method for preparing a capsule and a tablet as an oral pharmacological composition using the same.

BACKGROUND ART

Prostaglandins are known to play an important role in causing inflammation. Prostaglandins are produced from arachidonic acid by cyclooxygenase (hereinafter abbreviated as "COX"). The activity of COX is suppressed to inhibit the synthesis of prostaglandins, particularly, PGE2, PGG2, and PGH2, resulting in the treatment of inflammation.

Two COX isoenzymes, COX-1 and COX-2, are known. COX-1 is inherently found in the gastrointestinal tract and kidney and is assumed to maintain physiological homeostatic functions, including gastrointestinal integrity and renal functions. Inhibition of COX-1 activity may cause life-threatening toxicities, such as ulcers and hemorrhage in the gastrointestinal tract. In contrast, COX-2 is induced by inflammatory stimuli and is known to be responsible for the development of inflammation.

COX-2 inhibitors are assumed to possess a broad spectrum of therapeutic activities as well as anti-inflammatory, analgesic, and antipyretic activities. For example, inhibition of COX-2 is known to prevent the onset of cancers, particularly colorectal cancer [J. Clin. Invest., 99, 2254 (1997)], can apply to the treatment of chronic neurodegenerative diseases, such as Alzheimer's disease [Neurology, 48, 626 (1997)], and is also known to be useful in the reduction of infarct volume accompanied by a stroke [J. Neuroscience, 17, 2746 (1997)].

Conventional non-steroidal anti-inflammatory drugs (NSAIDs), such as indomethacin, naproxen, ketoprofen, ibuprofen, piroxicam, and diclofenac, inhibit both COX-1 and COX-2 to show gastrointestinal toxicities together with anti-inflammatory efficacy. Furthermore, such NSAIDs have fatal toxicities, such as hemorrhage and ulcers, arising from the inhibition of COX-1, limiting their clinical use. Thus, selective COX-2 inhibitors are useful as therapeutic agents against inflammation and diseases accompanied by inflammation without causing gastrointestinal toxicities, which are common during long-term use of conventional NSAIDs.

4,5-Diaryl-3(2H)-furanone derivatives have recently been reported as selective inhibitors against COX-2 (Korean Patent No. 10-0495389). Prior to use the furanone derivatives to prepare pharmaceutical compositions, the present inventors have derived an optimum crystalline structure through a study on stability depending on crystalline forms, and the compositions are required to have high dissolution rate, good flowability, optimum mass variation, and improved content uniformity. Therefore, the present inventors have found that a specific furanone derivative meets the requirements. Based on this finding, the present inventors have succeeded in preparing a capsule formulation and a tablet formulation using a pharmaceutical composition including the furanone derivative and finally arrived at the present invention.

DISCLOSURE

Technical Problem

It is one object of the present invention to provide a method for preparing furanone derivatives with excellent physicochemical stability and to prepare an oral pharmacological composition using the same. More specifically, the present invention is objected to provide a method for preparing furanone derivatives having a crystalline form A or G, or a mixed form thereof with excellent stability and to prepare a capsule and a tablet as an oral composition using the same.

Technical Solution

For this, the present inventors prepared a compound of Formula 1 or a pharmaceutically acceptable salt thereof having a crystalline form A or G (FIG. 1), or a mixed form thereof with excellent physicochemical stability:

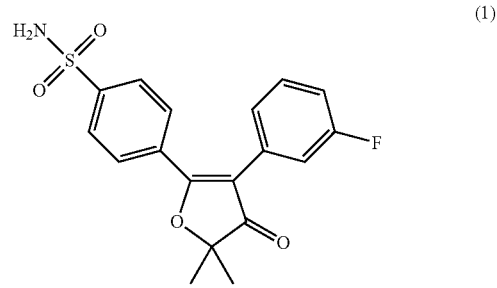 [SMILES: CC1(C)OC(c2ccc(S(N)(=O)=O)cc2)=C(c2cccc(F)c2)C1=O]

(1)

Further, in order to improve in-process flowability and secure high dissolution rate and uniform content, a median particle diameter at 50% in the cumulative distribution ($d_{(0.5)}$) and a median particle diameter at 90% in the cumulative distribution ($d_{(0.5)}$) were allowed to be maintained at 3 μm to 9 μm and 10 μm to 50 μm, respectively. Thus, one aspect of the present is to provide a pharmaceutical composition including the furanone derivative that meets such conditions, a pharmaceutically acceptable diluent, and a pharmaceutically acceptable lubricant.

Another aspect of the present invention is to provide a pharmaceutical formulation including the pharmaceutical composition.

Advantageous Effects

The pharmaceutical composition including 5-{4-(aminosulfonyl)phenyl}-2,2-dimethyl-4-(3-fluorophenyl)-3(2H)-furanone according to the present invention has the advantages of enhanced product stability, and high dissolution rate and excellent content uniformity due to uniform particle size within a given range during a manufacturing process. Due to these advantages, it can be prepared into an oral pharmacological composition of a constant level and as a non-steroidal anti-inflammatory drug, it may be effective in treating inflammation or pain.

MODE FOR INVENTION

The present invention will now be described in detail.

Figure 1:
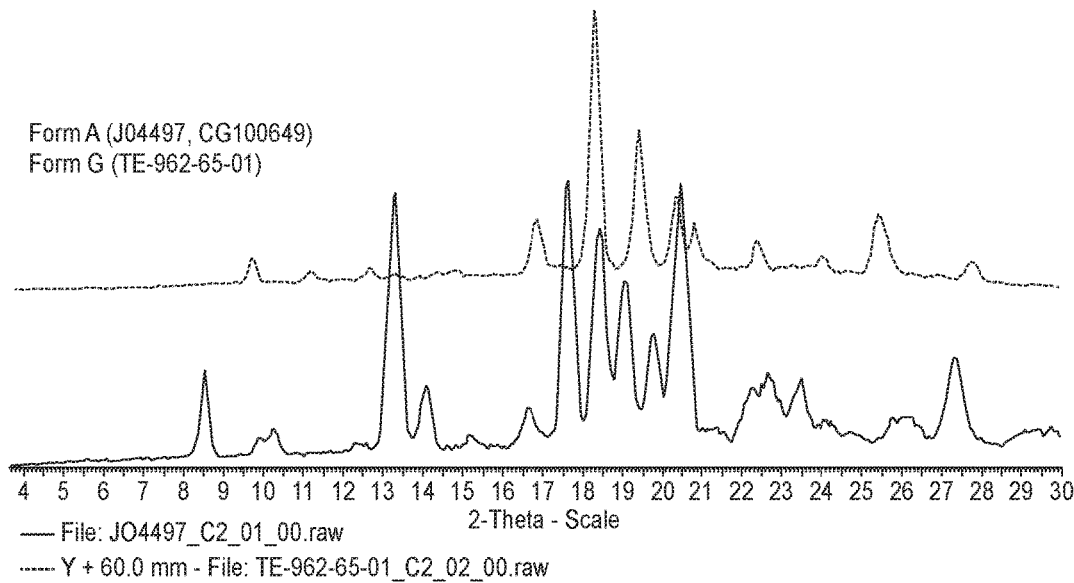
FIG. 1 is a graph showing the XRPD patterns for crystalline forms A and G.

The present invention provides a pharmaceutical composition including (i) the compound of Formula 1 or a pharmaceutically acceptable salt thereof having crystalline structures of a crystalline form A or G (FIG. 1), or a mixed form thereof and a 50% volume median particle diameter and 90% volume median particle diameter of 3 μm to 9 μm and 10 μm to 50 μm, respectively, (ii) a pharmaceutically acceptable diluent, and (iii) a pharmaceutically acceptable lubricant.

The compound of Formula 1 is used as an active ingredient in the pharmaceutical composition of the present invention. The compound of Formula 1 is a selective COX-2 inhibitor whose chemical name is "5-{4-(aminosulfonyl)phenyl}-2,2-dimethyl-4-(3-fluorophenyl)-3(2H)-furanone". The compound of Formula 1 is known to have reduced gastrointestinal toxicities and be effective against inflammatory diseases, inflammation-associated diseases, pain, solid cancers, angiogenesis-associated diseases, Alzheimer's disease, attacks, convulsions, strokes, and epilepsy over conventional NSAIDs (see Korean Patent No. 10-0495389).

Figure 12A:
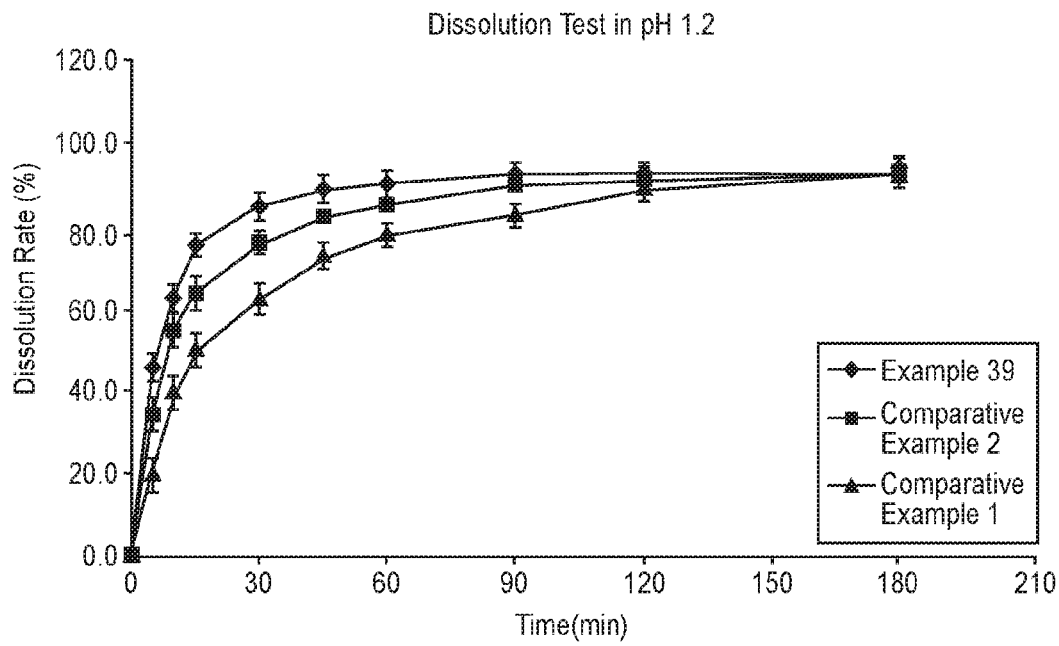
FIG. 12a is a graph showing the dissolution rates for crystalline forms of Example 39 and Comparative Examples 1 and 2 with eluting solution pH1.2.
Figure 12B:
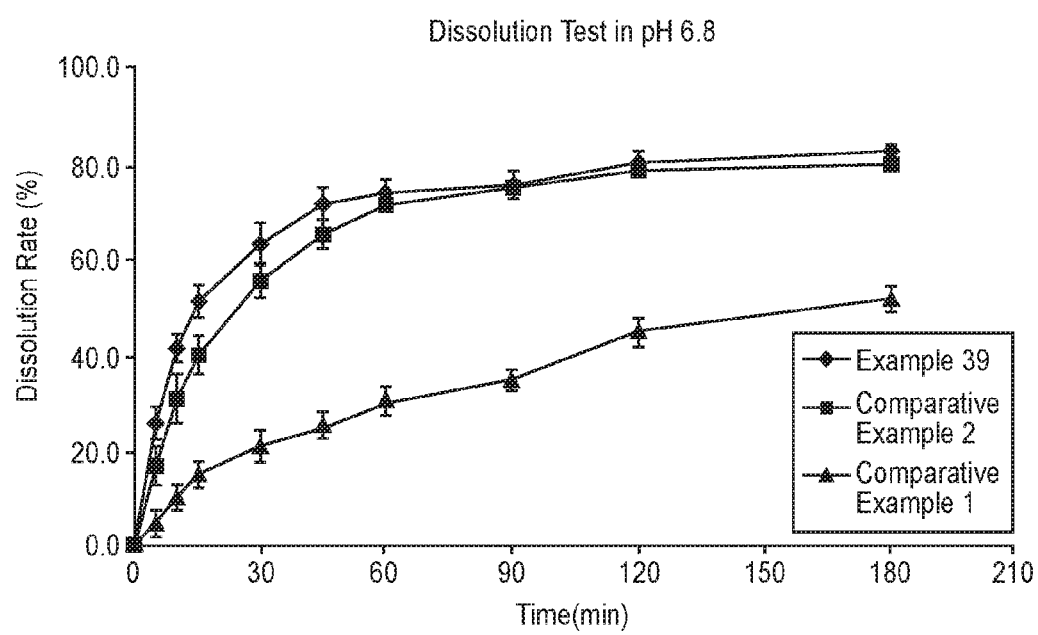
FIG. 12b is a graph showing the dissolution rates for crystalline forms of Example 39 and Comparative Examples 1 and 2 with eluting solution at pH6.8.

The compound of Formula 1 contained as an active ingredient in the pharmaceutical composition of the present invention is characterized by having crystalline structures of a crystalline form A or G (FIG. 1), or a mixed form thereof. Because the furanone derivative used as an active ingredient is used in a small amount of 0.5 to 20% by weight, based on the total weight of the pharmaceutical composition, when its 50% volume particle diameter ($d_{(0.5)}$) is 3 μm to 9 μm, and its 90% volume particle diameter ($d_{(0.9)}$) is 10 μm to 50 μm, it is easier to secure content uniformity of the compound when trituration is implemented using a diluent and a further improvement in the dissolution rate of the compound is attained (FIGS. 12a and 12b).

Further, the compound of Formula 1 used as an active ingredient in the pharmaceutical composition of the present invention may exist in the crystalline form A or the crystalline form G, or a mixed form thereof.

According to the results of experiments conducted by the present inventors, the crystalline form A and the crystalline form G were physicochemically stable. For example, when the two crystalline materials were put into a uncapped glass vial and stored in a chamber set to 25° C. and 97% (Relative Humidity) and 40° C. and 75% (Relative Humidity) for 7 days, appearance and crystalline structures of the compounds were remained unchanged, and creation of related substances was rarely observed. These results demonstrate that the crystalline forms A and G are remained physicochemically very stable. The present inventors obtained crystalline forms B to F (FIG. 2) by recrystallization of the crystalline form A from suitable solvents, such as t-butyl methyl ether, isopropyl alcohol, methyl alcohol, ethyl alcohol, and acetonitrile. However, the crystalline forms B to F tended to partially return to the crystalline form A during storage at 40° C. and 75% RH for 4 days. In contrast, the crystalline forms A and G were highly stable. Particularly, when the particles in the crystalline form A are present in a larger amount, specifically, when the crystalline form A is present in an amount of 50% by weight or more, based on the total weight of the crystalline forms, a higher dissolution rate was obtained. Accordingly, in the present invention, it is preferred that the compound of Formula 1 includes at least 50% by weight of the crystalline form A, based on the total weight of the compound.

The states of the crystalline forms A and G are maintained stable during long-term storage under accelerated storage conditions.

The compound of Formula 1 may be used in an amount of 0.5 to 20% by weight, preferably 1% to 2% by weight, based on the total weight of the pharmaceutical composition.

The compound of Formula 1 may exist in the form of a pharmaceutically acceptable salt.

The pharmaceutical composition of the present invention includes a pharmaceutically acceptable diluent and a pharmaceutically acceptable lubricant in addition to the active ingredient.

The diluent may be used in an amount of 75 to 99% by weight, based on the total weight of the pharmaceutical composition. As the diluent, there may be mentioned, for example, silicified microcrystalline cellulose (e.g., silicified microcrystalline cellulose 50 or 90), microcrystalline cellulose, cellulose, lactose or a combination thereof (e.g., Cellactose® 80). The use of silicified microcrystalline cellulose is preferred.

The lubricant may be used in an amount of 0.1 to 5% by weight, preferably 1% by weight, based on the total weight of the pharmaceutical composition. As the lubricant, there may be mentioned, for example, talc or stearic acid. The use of talc is preferred.

The pharmaceutical composition of the present invention may further include one or more pharmaceutically acceptable additives commonly used in the pharmaceutical art, in addition to the diluent and the lubricant.

The pharmaceutical composition can be used for the prevention or treatment of inflammatory diseases, inflammation-associated diseases, pain, solid cancers, angiogenesis-associated diseases, Alzheimer's disease, attacks, convulsions, strokes or epilepsy. The pharmaceutical composition is preferably used for the prevention or treatment of inflammatory diseases, inflammation-associated diseases or pain.

The pharmaceutical composition of the present invention can be processed into various pharmaceutical formulations.

The formulations may be in the form of tablets, powders, granules, soft and hard capsules, suspensions, inhalation sprays, and injectable solutions. The formulations are preferably capsules and tablets.

The pharmaceutical composition of the present invention may be administered via various routes, including but not limited to, orally, intravenously, subcutaneously, and by topical application.

The pharmaceutical composition of the present invention including the compound of Formula 1 may be administered in a daily dose of 0.1 to 100 mg/kg body weight to a patient. The daily dose may vary depending on the indication, condition or state of the patient. The pharmaceutical composition of the present invention may be administered according to various schedules, such as once, twice, and three times a day, but is not limited to these schedules.

The present invention will be explained in detail with reference to the following examples, including test examples. However, these examples are provided for illustrative purposes only and are not intended to limit the scope of the invention.

5-{4-(Aminosulfonyl)phenyl}-2,2-dimethyl-4-(3-fluorophenyl)-3(2H)-furanone of Formula 1 was prepared in accordance with the procedure described in Example 4 of Korean Patent No. 10-0495389.

Figure 2:
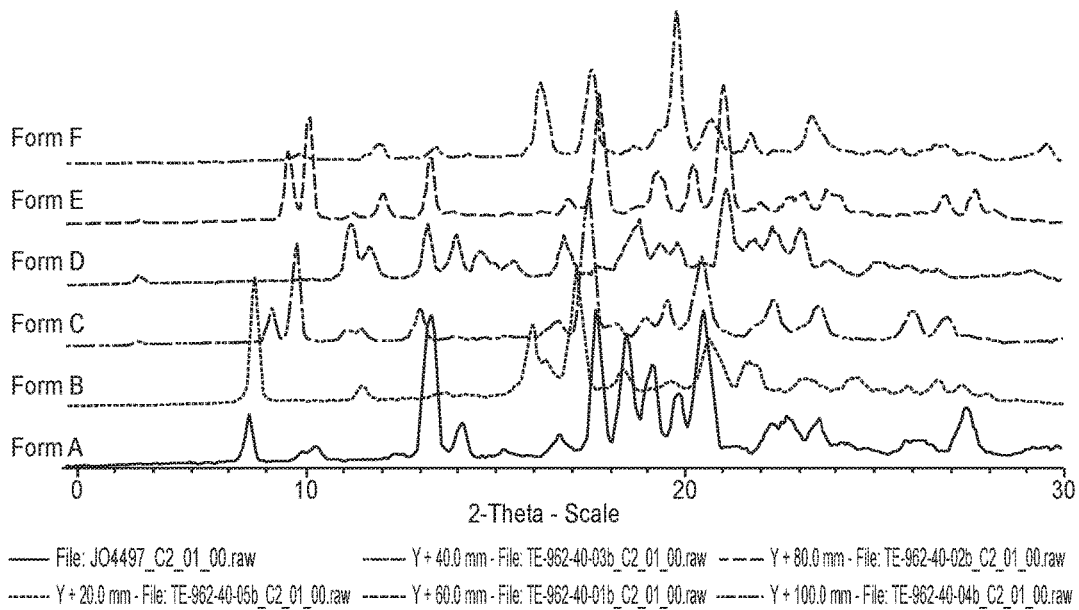
FIG. 2 is a graph showing the XRPD patterns for crystalline forms A, B, C, D, E and F.

Preparative Example 1: Solubility test for 5-{4-(aminosulfonyl)phenyl}-2,2-dimethyl-4-(3-fluorophenyl)-3(2H)-furanone and Identification of Crystalline Form Thereof after Evaporation Drying As can be seen from Table 1, about 5 mg of the synthesized 5-{4-(aminosulfonyl)phenyl}-2,2-dimethyl-4-(3-fluorophenyl)-3(2H)-furanone was dissolved in solvents, i.e., water, acetone, t-butyl alcohol (tBuOH), DCM (Dichloromethane) and tert butyl methyl ether (TBME) and whether the compound is dissolved in the solvents or not was observed. At this time, the amount of the solvents was gradually increased up to the volume corresponding to 200 times of the amount used of the raw material. Then, the solvents were evaporated at room temperature for drying and XRPD patterns of the obtained dried materials were confirmed. Each XRPD pattern is shown in FIG. 2.

TABLE 1

| | Solvent | 10 vol (50 uL) | 20 vol (100 uL) | 40 vol (200 uL) | 60 vol (300 uL) | 80 vol (400 uL) | 100 vol (500 uL) | 200 vol (1000 uL) | Observation after solvent evaporation | XRPD |
|---|---|---|---|---|---|---|---|---|---|---|
| Example 1 | Water | X | X | X | X | X | X | X | Yellow solid | Form A |
| Example 2 | Acetone | ○ | | | | | | | Yellow solid | Form A |
| Example 3 | tBuOH | X | X | Δ | Δ | Δ | Δ | Δ | Yellow solid | Form A |
| Example 4 | DCM | X | X | Δ | Δ | Δ | ○ | | Yellow solid | Form A |
| Example 5 | TBME | X | X | X | X | X | X | X | Yellow solid | Form B |

X: not dissolved;
Δ: Partially dissolved;
○: Dissolved

Preparation Example 2: Preparation of Anhydrous Form of 5-{4-(aminosulfonyl)phenyl}-2,2-dimethyl-4-(3-fluorophenyl)-3(2H)-furanone 5-{4-(Aminosulfonyl)phenyl}-2,2-dimethyl-4-(3-fluorophenyl)-3(2H)-furanone was prepared in accordance with the procedure described in Example 4 of Korean Patent No. 10-0495389. Then, about 18 g of the compound was dissolved in 200 mL of acetone. The completely dissolved solution was vacuum dried at 40° C. using a rotary evaporator (Buchi Rota Vapour R200). The compound thus obtained was a sponge-like solid. When the compound was stored at room temperature for a long period, the structure of the crystalline form A was gradually formed, and related substances were created due to hygroscopic property. Thus, the compound was physicochemically unstable.

Preparation Example 3: Solubility test for 5-{4-(aminosulfonyl)phenyl}-2,2-dimethyl-4-(3-fluorophenyl)-3(2H)-furanone and Screening of Crystalline Form Thereof 5-{4-(Aminosulfonyl)phenyl}-2,2-dimethyl-4-(3-fluorophenyl)-3(2H)-furanone was prepared in accordance with the procedure described in Example 4 of Korean Patent No. 10-0495389. Then, about 50 mg of the compound was dissolved in 28 kinds of single solvent or a mixture thereof while heating to 50° C. and whether the compound is dissolved in the solvent or not was observed. At this time, the amount of the solvents was gradually increased up to the volume corresponding to 100 times of the amount used of the raw material.

When dissolution was incomplete during the experiment, the solution was maturated by repeatedly heating to 50° C. and then cooling to room temperature 8 times for 24 hr in an incubation chamber. After maturation, the solvent was dried at room temperature.

During the experiment, the completely dissolved solution was stored under a cold condition (4° C.) for 24 hr to allow crystal formation, recovered and dried at room temperature. Then XRPD analysis was performed. In the case of N-methylpyrolidone (NMP), a solid was not formed even though dried at room temperature for 19 days after cold storage.

As can be seen from Table 2, the experiment results showed that 5-{4-(Aminosulfonyl)phenyl}-2,2-dimethyl-4-(3-fluorophenyl)-3(2H)-furanone was dissolved in acetone, 2-butanone, THF, DMSO, Methylpyrrolidine, Dioxane, acetonitrile aqueous solution, NMP and 1-methoxy-IPA in the volume of the solvents corresponding to 10 times of the amount used of the raw material, and the compound was dissolved in ethyl acetate, acetonitrile, MIBK, DCM, Nitromethane in the volume of the solvents corresponding to 20 times to 40 times of the amount used of the raw material. However, the compound was not dissolved in IPA, Toluene, TBME, Diethyl ether, Heptane and water even though the volume of the solvent was increased up to 100 times of the amount used of the raw material and the solution was heated up to 50° C. The resulting materials, except NMP, formed pale yellow or yellowish solids after drying, and the results of pattern analysis using XPRD analysis showed that different crystalline structures were obtained depending on the solvent used. As can be seen from Table 2, the mixed crystalline forms, Form D+Form A and Form E+Form A, were obtained when methanol and ethanol were used as a solvent, respectively, and the Form B was obtained when the 5-{4-(Aminosulfonyl)phenyl}-2,2-dimethyl-4-(3-fluorophenyl)-3(2H)-furanone was treated with TBME. The crystalline Form C was obtained when the synthesized furanone derivative was treated with IPA or its aqueous solution and then dried. As can be seen from Table 2, the Form A was formed in the case of 1-propanol, acetone, ethyl acetate, acetonitrile, toluene, Isopropyl acetate, 2-butanone, THF, DMSO, Methylpyrrolidine, Diethyl ether, MIBK, DCM, Heptane, Dioxane, Nitromethane, ethanol aqueous solution, acetonitrile aqueous solution, water, ethylene glycol, 1-methoxy-IPA.

TABLE 2

| | Solvent | 10 vol (r.t) | 10 vol (50° C.) | 20 vol (r.t) | 20 vol (50° C.) | 40 vol (r.t.) | 40 vol (50° C.) | 60 vol (r.t.) | 60 vol (50° C.) | 80 vol (r.t.) | 80 vol (50° C.) | 100 vol (r.t.) | 100 vol (50° C.) |
|---|---|---|---|---|---|---|---|---|---|---|---|---|---|
| Example 6 | Methanol | X,# | X | X | X | X | Δ | Δ | O | Δ | O | O | |
| Example 7 | Ethanol | X,# | X | X | X | X | Δ | Δ | O | O | | | |
| Example 8 | IPA | X,# | X | X | X | X | X | X | Δ | Δ | Δ | Δ | |
| Example 9 | I-propanol | X | X | X | X | X | | | | | | | |
| Example 10 | Acetone | O | | | | | | | | | | | |
| Example 11 | Ethyl acetate | X | Δ | O | | | | | | | | | |
| Example 12 | Acetonitrile | X,# | X | Δ | O | | | | | | | | |
| Example 13 | Toluene | X | X | X | X | X | X | X | X | X | X | X | X |
| Example 14 | Isopropyl acetate | X | X | X | Δ | O | O | | | | | | |
| Example 15 | TBME | X | X | X | X | X | X | X,# | X | X | X | X | X |
| Example 16 | 2-butanone | O | | | | | | | | | | | |
| Example 17 | THF | O | | | | | | | | | | | |
| Example 18 | DMSO | O | | | | | | | | | | | |
| Example 19 | Methylpyrrolidine | O | | | | | | | | | | | |
| Example 20 | Diethyl ether | X | X | X | X | X | X | X | X | X | X | X | X |
| Example 21 | Methyl isobutyl ketone | X | X | Δ | O | O | | | | | | | |
| Example 22 | DCM | X | X | X | Δ | O | O | | | | | | |
| Example 23 | Heptane | X | X | X | X | X | X | X | X | X | X | X | X |
| Example 24 | Dioxane | O | | | | | | | | | | | |
| Example 25 | Nitromethane | X | Δ | Δ | O | O | | | | | | | |
| Example 26 | 90% EtOH aq. sol. | X | X | X | X,# | Δ | O | Δ | O | O | O | | |
| Example 27 | 90% ACN aq. sol. | O | | | | | | | | | | | |
| Example 28 | 90% IPA aq. sol. | X | X | X | X | X | X | X | Δ | X | Δ | Δ | Δ |
| Example 29 | 90% Acetone aq. sol. | O | | | | | | | | | | | |
| Example 30 | Water | X | X | X | X | X | X | X | X | X | X | X | X |
| Example 31 | Ethylene glycol | X | X | X | X | X | Δ | X | Δ | Δ | Δ | Δ | Δ |
| Example 32 | NMP | O | | | | | | | | | | | |
| Example 33 | 1-methoxy-IPA | O | | | | | | | | | | | |

| | Solvent | Cooling after 24 hrs | Maturation after 24 hrs | Evaporation | XRPD |
|---|---|---|---|---|---|
| Example 6 | Methanol | Few crystals | — | Pale yellow solid | Mixture: Form D + Form A |
| Example 7 | Ethanol | Few crystals | — | Pale yellow solid | Mixture: From E + Form A |
| Example 8 | IPA | — | Solution | White solid | Form C |
| Example 9 | 1-propanol | Solution | — | Yellow solid | Form A |
| Example 10 | Acetone | Solution | — | Yellow solid | Form A |
| Example 11 | Ethyl acetate | Solution | — | Yellow solid | Form A |
| Example 12 | Acetonitrile | Few crystals | — | Yellow solid | Form A |
| Example 13 | Tolune | — | Suspension | Yellow solid | Form A |
| Example 14 | Isopropyl acetate | Solution | — | Yellow solid | Form A |
| Example 15 | TBME | — | — | Yellow solid | Form B |
| Example 16 | 2-butanone | Solution | — | Yellow solid | Form A |
| Example 17 | THF | Solution | — | Yellow solid | Form A |
| Example 18 | DMSO | Solution | — | Yellow solid | Form A |

TABLE 2-continued

| | | | | | |
|---|---|---|---|---|---|
| Example 19 | Methylpyrrolidine | Solution | — | Yellow solid | Form A |
| Example 20 | Diethyl ether | — | Yellow solid | Yellow solid | Form A |
| Example 21 | Methyl isobutyl | Solution | — | Yellow solid | Form A |
| Example 22 | DCM | Solution | — | Yellow solid | Form A |
| Example 23 | Heptane | — | Suspension | Yellow solid | Form A |
| Example 24 | Dioxane | Solution | — | Yellow solid | Form A |
| Example 25 | Nitromethane | Solution | — | Yellow solid | Form A |
| Example 26 | 90% EtOH aq. | Solution | — | Yellow solid | Form A |
| Example 27 | 90% CAN aq. sol. | Few Crystals | — | Yellow solid | Form A |
| Example 28 | 90% IPA aq. Sol. | — | Solution | Yellow solid | Form C |
| Example 29 | Aq. sol. | Solution | — | Yellow solid | Form A |
| Example 30 | Water | — | Suspension | Yellow solid | Form A |
| Example 31 | Ethylene glycol | — | Suspension | Yellow solid | Form A |
| Example 32 | NMP | Solution | — | Yellow solid | — |
| Example 33 | 1-methoxy-IPA | Solution | — | Yellow solid | Form A |

Preparation Example 4: Preparation of Crystalline Forms B to F of 5-{4-(aminosulfonyl)phenyl}-2,2-dimethyl-4-(3-fluorophenyl)-3(2H)-furanone About 500 mg of 5-{4-(Aminosulfonyl)phenyl}-2,2-dimethyl-4-(3-fluorophenyl)-3(2H)-furanone was mixed with solvents (Table 3) in about 5 ml to 30 ml corresponding to 10 times to 60 times of the amount used of the raw material, and stirred at room temperature until white precipitates were formed. The precipitates were filtered and vacuum dried at 25° C. for 3 hr. A part of the solid primarily obtained showed yellowish color. In order to remove the solid, secondarily, the solid was put into 5 ml to 30 ml of organic solvents again and then stirred at room temperature for 3 hr until white precipitates were formed. The precipitates were filtered and then vacuum dried to obtain a white solid. Finally, crystalline form of the obtained solid was confirmed by XRPD analysis. Methods for manufacturing each crystalline form and the crystalline forms of the compounds prepared by the methods are shown in Table 3. The obtained crystalline forms were called "crystalline forms B, C, D, E and F".

TABLE 3

| | Solvent | Volume of solvent used in the suspension | XRPD |
|---|---|---|---|
| Example 34 | Methanol | 10 vol. (5 mL) | Form D |
| Example 35 | Ethanol | 10 vol. (5 mL) | Form E |
| Example 36 | IPA | 10 vol. (5 mL) | Form C |
| Example 37 | Acetonitrile | 10 vol. (5 mL) | Form F |
| Example 38 | TBME | 60 vol. (30 mL) | Form B |

Preparative Example 5: Preparation of 5-{4-(aminosulfonyl)phenyl}-2,2-dimethyl-4-(3-fluorophenyl)-3(2H)-furanone and Characterization of Crystalline Form Thereof (Crystalline Form A)

5-{4-(Aminosulfonyl)phenyl}-2,2-dimethyl-4-(3-fluorophenyl)-3 (2H)-furanone was prepared in accordance with the procedure described in Example 4 of Korean Patent No. 10-0495389.

Specifically, 4-bromo-2,2-dimethyl-5-4-(aminosulfonyl) phenyl-3 (2H)-furanone (170 mg) was dissolved in 30 mL of toluene and 10 mL of ethanol. The solution was stirred. To the solution were added dropwise 25 mg of tetrakis (triphenylphosphine) palladium (0), 10 mL of a saturated aqueous solution of sodium bicarbonate, and 100 mg of 3-fluorobenzeneboronic acid. After stirring at 90° C. for 12 hr, the solvents were removed from the reaction solution under reduced pressure and the residue was extracted with water and dichloromethane. The organic layer was concentrated under reduced pressure and the residue was purified by column chromatography (hexane/ethyl acetate), yielding 120 mg of 5-{4-(aminosulfonyl)phenyl}-2,2-dimethyl-4-(3-fluorophenyl)-3(2H)-furanone as a solid.

(1) X-Ray Diffraction (XRD) Analysis

After the compound prepared in Preparative Example 5 was crystallized by a general crystallization method, its crystalline form was characterized by X-ray diffraction (XRD) analysis. The XRD analysis was performed using an Ultima III high-resolution X-ray diffractometer (Rigaku, Japan) with Cu radiation.

The experimental results are shown in Table 4.

TABLE 4

The crystalline form of the compound prepared in Preparative Example 5

| 2θ | Intensity (cps) |
|---|---|
| 8.40 | 7125 |
| 13.26 | 10050 |
| 14.02 | 2612 |
| 17.70 | 12200 |
| 18.48 | 10388 |
| 19.14 | 7400 |
| 19.84 | 5150 |
| 20.54 | 11750 |
| 22.72 | 2788 |
| 23.56 | 3100 |
| 27.62 | 3088 |

(2) Differential Scanning Calorimetry (DSC)

The crystalline form of the compound prepared in Preparative Example 5 was analyzed by differential scanning calorimetry (DSC). The DSC analysis was performed using a DSC 823e (Mettler Toledo, Switzerland). About 1 mg to 2.3 mg of a sample of the crystalline form was placed on an aluminum pan and heated at a rate of 10° C./min from 25° C. to 220° C. The data were analyzed with the STARe v9.20 (Proteus®).

Figure 3:
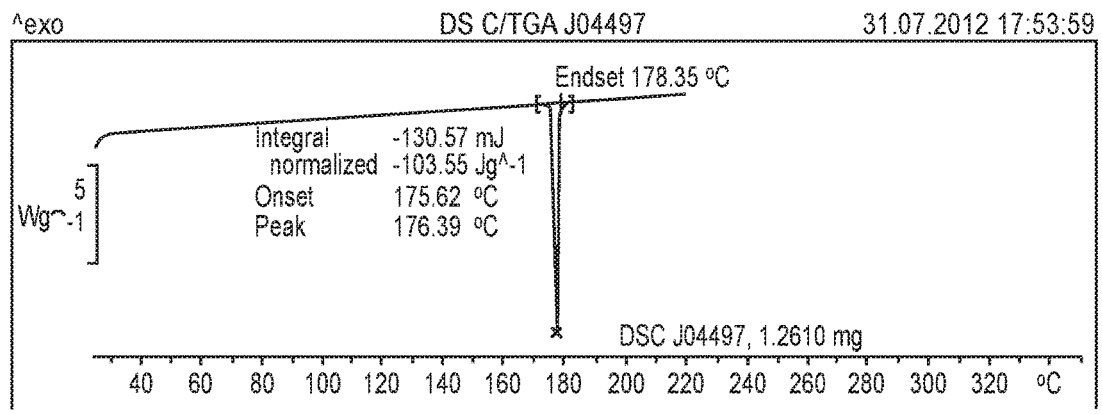
FIG. 3 is a graph showing the results of differential scanning calorimetry (DSC) for a crystalline form prepared in Preparative Example 5.

The experimental results are shown in FIG. 3.

The crystalline form of the compound prepared in Preparative Example 5 with the results of XRD and DSC analyses was called "crystalline form A".

Preparative Example 6: Preparation of Crystalline Form G of 5-{4-(aminosulfonyl)phenyl}-2,2-dimethyl-4-(3-fluorophenyl)-3(2H)-furanone The crystalline form G of 5-{4-(aminosulfonyl)phenyl}-2,2-dimethyl-4-(3-fluorophenyl)-3(2H)-furanone was prepared by using a DSC instrument (Q2000, TA Instruments, UK or DSC 823e, Mettler Toledo, Switzerland) for changing crystalline form in addition to a melt crystallization method. Specifically, 5 mg of a sample of the crystalline form A prepared in Preparative Example 5 was placed on an aluminum pan and subjected to a heating-isothermal-cooling cycle in a TA instrument to prepare a new crystalline form. The cycle consisted of five stages: heating at a rate of 10° C./min from 25° C. to 180° C. (stage 1); maintenance at 180° C. for 5 min (stage 2); cooling at a rate of 10° C./min from 180° C. to 25° C. (stage 3); maintenance at 25° C. for 1 min (stage 4); and heating at a rate of 10° C./min from 25° C. to 170° C. (stage 5). Throughout the preparation of the crystalline form of the compound, nitrogen purging was maintained at 50 ml/min.

(1) X-Ray Diffraction (XRD) Analysis

The crystalline form of the compound prepared in Preparative Example 6 was characterized by X-ray diffraction (XRD) analysis. The XRD analysis was performed using an Ultima III high-resolution X-ray diffractometer (Rigaku, Japan) with Cu radiation.

The experimental results are shown in Table 5.

TABLE 5

The crystalline form of the compound prepared in Preparative Example 6

| 2θ | Intensity (cps) |
| --- | --- |
| 11.10 | 3112 |
| 12.66 | 8762 |
| 16.92 | 7812 |
| 18.26 | 18038 |
| 19.48 | 8288 |
| 20.80 | 9775 |
| 22.46 | 4775 |
| 24.02 | 5350 |
| 25.42 | 17138 |
| 27.76 | 4700 |

(2) Differential Scanning Calorimetry (DSC)

The crystalline form of the compound prepared in Preparative Example 6 was analyzed by differential scanning calorimetry (DSC). The DSC analysis was performed using a DSC 823e (Mettler Toledo, Switzerland). About 1 mg to 2.3 mg of a sample of the crystalline form was placed on an aluminum pan and heated at a rate of 10° C./min from 25° C. to 220° C. The data were analyzed with the STARe v9.20 (Proteus®).

Figure 4:
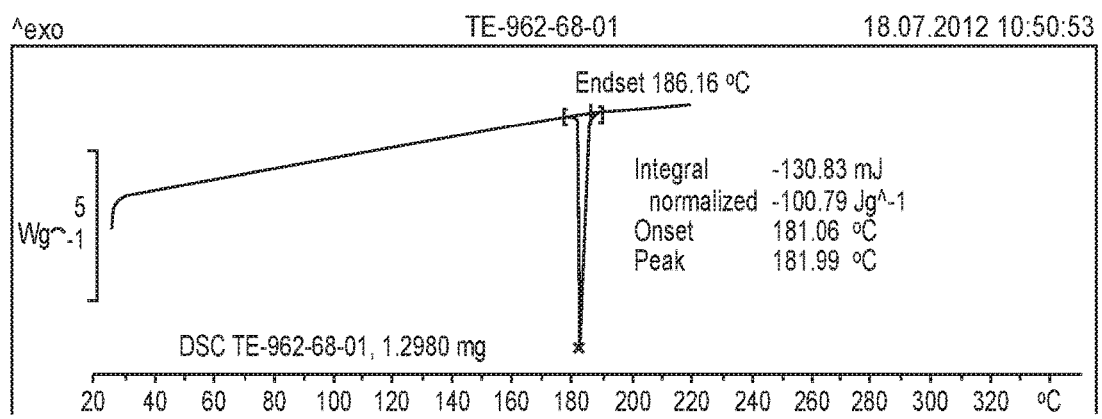
FIG. 4 is a graph showing the results of differential scanning calorimetry (DSC) for a crystalline form prepared in Preparative Example 6.

The experimental results are shown in FIG. 4.

The results of the XRD and DSC analyses confirm that the crystalline form of the compound prepared in Preparative Example 6 is quite different from the crystalline form A of the compound prepared in Preparative Example 5. The crystalline form of the compound prepared in Preparative Example 6 with the results of XRD and DSC analyses was called "crystalline form G".

Preparative Example 7: Preparation and Characterization of Mixture of the Crystalline Forms (Crystalline Form A+Crystalline Form G) of 5-{4-(aminosulfonyl)phenyl}-2,2-dimethyl-4-(3-fluorophenyl)-3(2H)-furanone The crystalline forms of Preparative Examples 5 and 6 were mixed in a weight ratio of 50:50 to prepare a mixture. The mixture was characterized to investigate whether the characteristics of the crystalline forms were maintained.

The mixture of the crystalline forms A and G was analyzed by differential scanning calorimetry (DSC). The DSC analysis was performed using DSC 200 F3 Maia® (NETZSCH). About 1 mg to 5 mg of a sample of the mixture was placed on an aluminum pan and heated at a rate of 20° C./min from 25° C. to 100° C. and at a rate of 10° C./min from 100° C. to 250° C. The data were analyzed with the STARe v9.20 (Proteus®).

Figure 5:
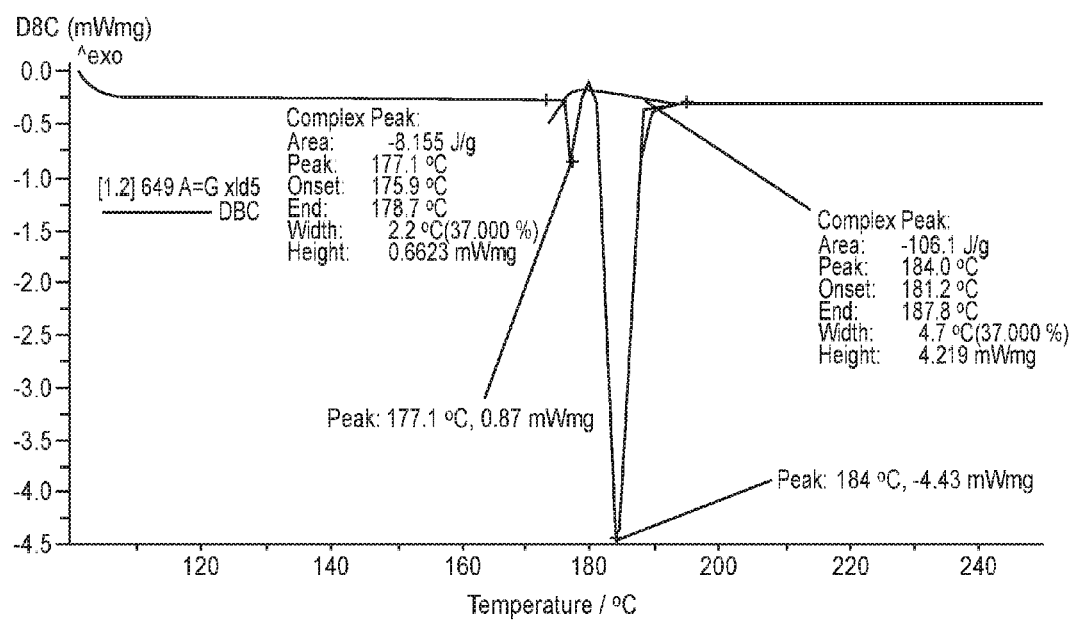
FIG. 5 is a graph showing the results of differential scanning calorimetry (DSC) for a crystalline form prepared in Preparative Example 7.

The experimental results are shown in FIG. 5.

As shown in FIG. 5, the DSC graph of the mixture of the crystalline forms prepared in Preparative Example 7 reveals the endothermic peaks corresponding to the crystalline forms of Preparative Examples 5 and 6. These results show that the crystalline forms A and G maintain their characteristics even when mixed.

Figure 6:
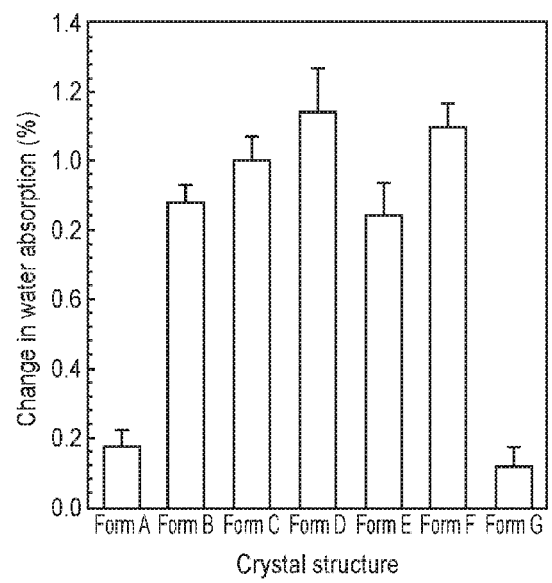
FIG. 6 is a graph showing water content levels according to crystalline structures.

Test Example 1: Analysis of Hygroscopic Property and Physicochemical Stability of Different Crystalline Forms Physicochemical stability of the crystalline furanone derivatives prepared by the methods mentioned above were confirmed at different storage conditions. The physicochemical stability was evaluated by water content and degree of related substance creation. For this, unpacked raw materials having different crystalline forms were stored under 25±2° C. and 75±5% (RH) condition for 72 hr. Then, water content in each raw material itself was measured and compared. The results are shown in FIG. 6. The water contents of the crystalline forms A and G were 0.2% or less, but the water contents of the five crystalline forms B to F were highly increased compared to the crystalline forms A and G as much as about 0.8% to 1.2%. As can be seen from FIGS. 1 and 2, it is thought that water hardly penetrates into the raw materials having the crystalline forms A and G due to higher degree of crystallinity of the crystalline forms A and G than the crystalline forms B to F, and therefore, the crystalline forms A and G are hardly absorb water.

Figure 7:
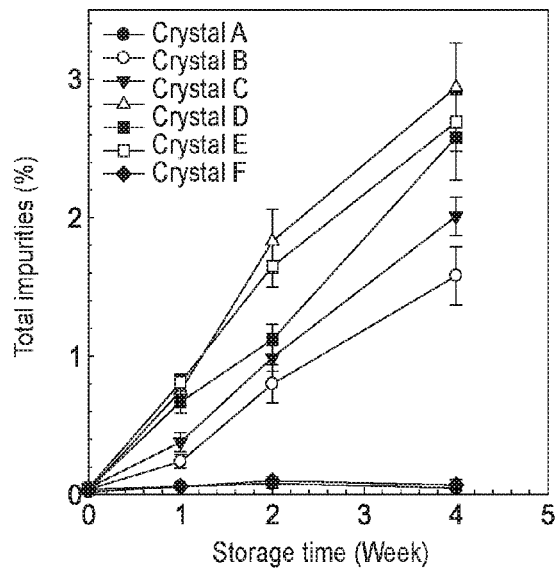
FIG. 7 is a graph showing the degrees of related substance creation under stress conditions according to crystalline structures.

Stability of the 5-{4-(aminosulfonyl)phenyl}-2,2-dimethyl-4-(3-fluorophenyl)-3(2H)-furanone compound was evaluated by evaluating the degree of related substance creation at different storage periods while storing the compound under stress conditions (60±2° C. and 85±5% (RH)). Each raw material was sealed in a glass vial and sampled at different elapsed time. The samples were evaluated by HPLC analysis. The results are shown in FIG. 7. As can be seen from the results, the crystalline forms A and G maintained the total related substance constantly as much as about 0.1% under stress conditions even after 4 week storage. However, the crystalline forms B, C, D, E and F showed similar level of the total related substance with the crystalline forms A and G at the beginning, but the level was rapidly increased under stress conditions over time. Based on the above results, the crystalline forms A and G were selected and used for the study for manufacturing an oral pharmacological composition.

Additionally, the crystalline forms of the compound of Formula 1 were evaluated for storage stability. The crystalline form A of Preparative Example 5 and the crystalline form G of Preparative Example 6 were filled in different hard capsules and stored under severe humidity conditions (25° C./97% RH) and accelerated storage conditions (40° C./75% RH) for 7 days. X-ray diffraction analysis was performed in accordance with the same method as described in Preparative Examples 5 and 6.

Figure 8A:
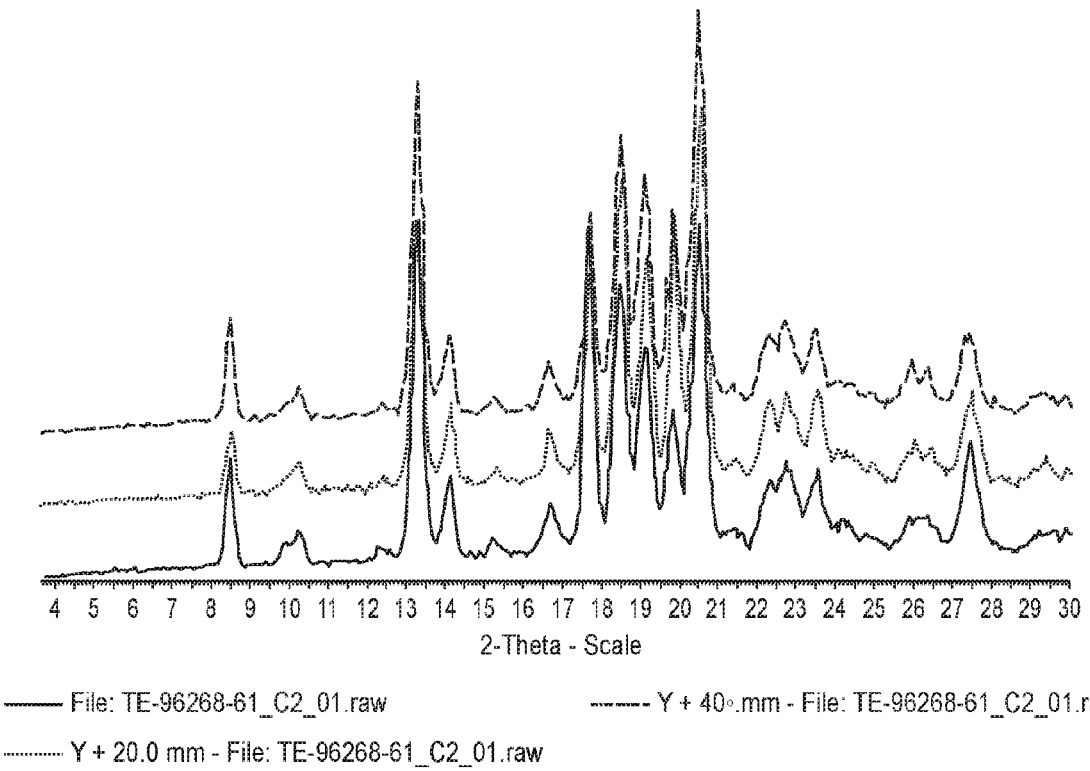
FIG. 8a shows the results of X-ray diffraction analysis for crystalline forms prepared in Preparative Example 5 after storage under different conditions.
Figure 8B:
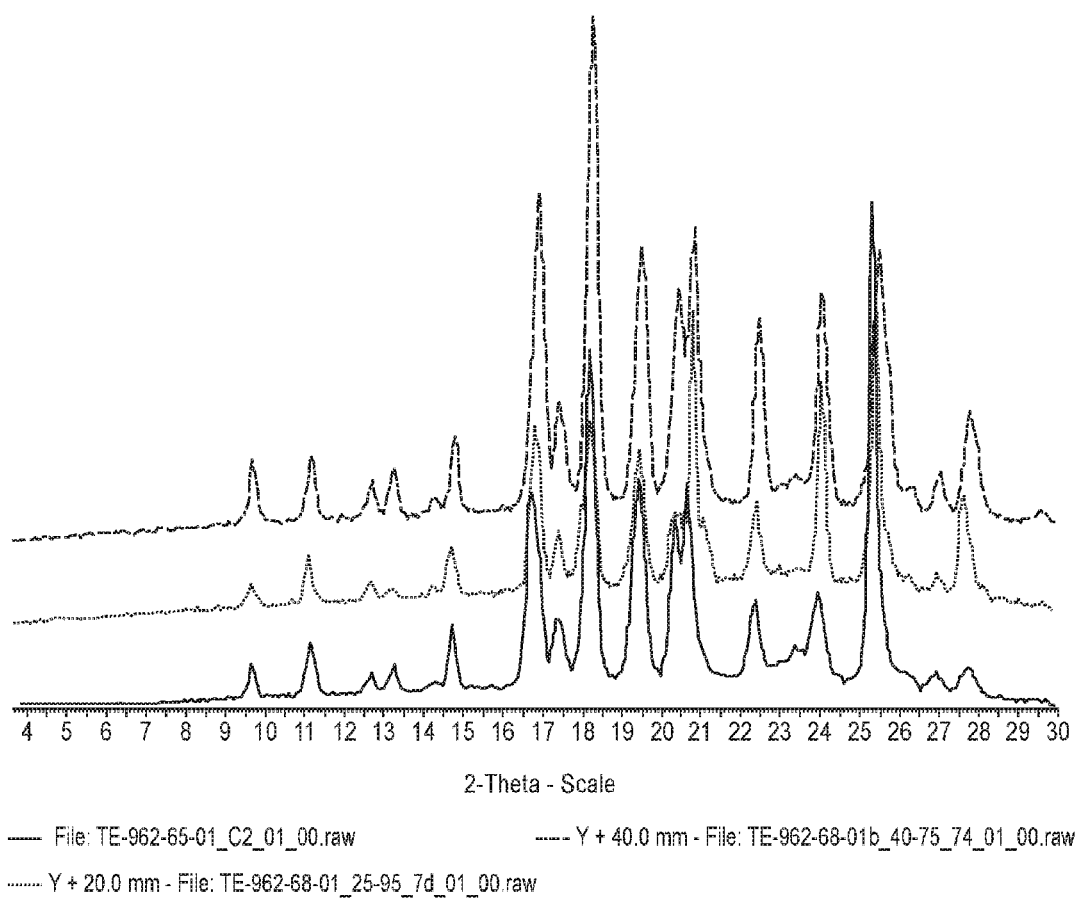
FIG. 8b shows the results of X-ray diffraction analysis for crystalline forms prepared in Preparative Example 6 after storage under different conditions.

The results of analysis are shown in FIGS. 8a and 8b.

As can be seen from FIGS. 8a and 8b, the states of the crystalline forms A and G of the compound of Formula 1 were maintained stable under severe humidity conditions and accelerated storage conditions.

Test Example 2: Analysis of Dissolution Rates of Different Crystalline Forms

In this example, the dissolution rates of the crystalline forms of the compound of Formula 1 were examined. Specifically, each of the crystalline form A of Preparative Example 5 and the crystalline form G of Preparative Example 6 was filled in hard capsules and was then eluted in 900 ml of a pH 1.2 solution at different revolution numbers of 50 and 100 rpm and a temperature of 37±0.5° C. for 2 hr. The eluted particles were analyzed under the following HPLC conditions:

<Hplc Conditions>
Column: Hypurity C18, 250×4.6 mm, 5 μm or its equivalent column
Detector: UV absorption spectrometer (measured at 325 nm)
Injection volume: 100 μl
Flow rate: 1.5 ml/min
Column temperature: 30° C.
Mobile phase: A—acetonitrile, B—water, A:B=60:40, v/v %
Analysis time: 5 min The experimental results obtained at revolution numbers of 50 rpm and 100 rpm are shown in FIGS. 9a and 9b, respectively.

Figure 9A:
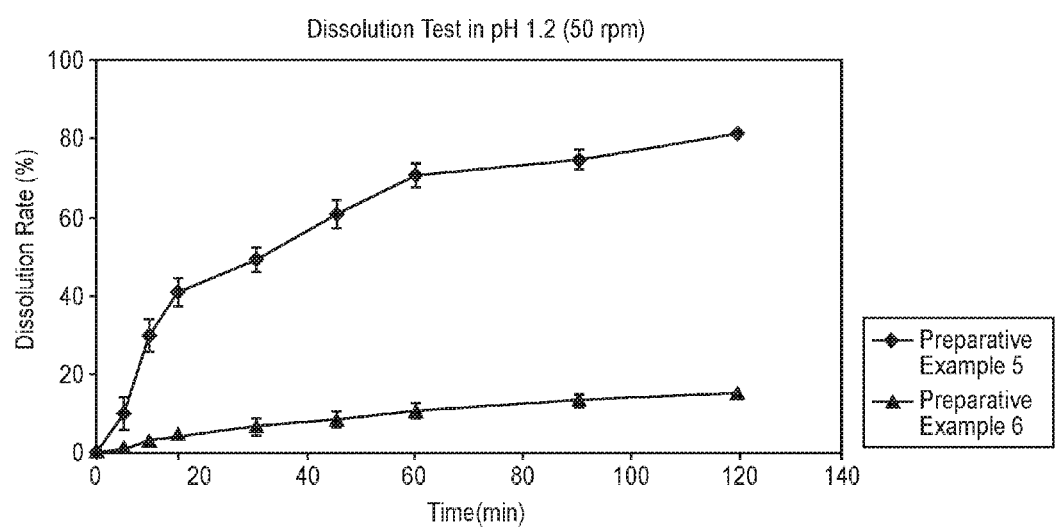
FIG. 9a is a graph showing the dissolution rates for crystalline forms prepared in Preparative Examples 5 and 6 at a revolution number of 50 rpm.
Figure 9B:
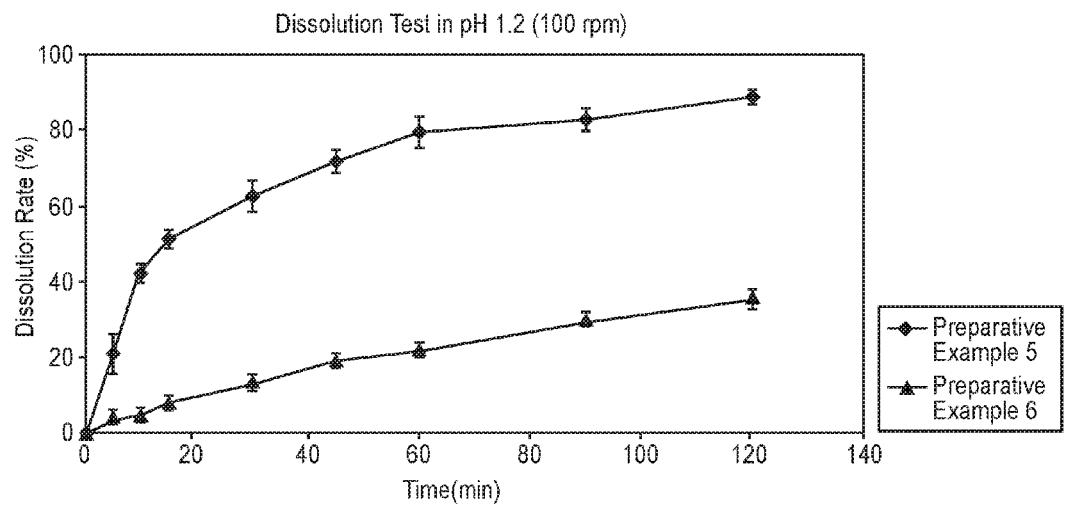
FIG. 9b is a graph showing the dissolution rates for crystalline forms prepared in Preparative Examples 5 and 6 at a revolution number of 100 rpm.

As can be seen from FIGS. 9a and 9b, the crystalline form A showed higher dissolution rates than the crystalline form G at the two different revolution numbers. These results demonstrate that the crystalline forms of the compound of Formula 1 exhibit different dissolution rates and a large proportion of the crystalline form A would be advantageous in achieving a desired dissolution rate. Higher dissolution rates of formulations containing larger proportions of the crystalline form A were confirmed in Preparative Examples 8 to 11.

Preparative Examples 8 to 11: Production of Particles of Mixtures Containing Crystalline Forms in Different Ratios The crystalline form A of Preparative Example 5 and the crystalline form G of Preparative Example 6 were mixed in the ratios shown in Table 6. The dissolution rates of the mixtures were investigated.

TABLE 6

|  | Preparative Example 8 | Preparative Example 9 | Preparative Example 10 | Preparative Example 11 |
|---|---|---|---|---|
| Crystalline form A (wt %) | 30 | 50 | 70 | 90 |
| Crystalline form G (wt %) | 70 | 50 | 30 | 10 |
| Total amount (%) | 100 | 100 | 100 | 100 |

Test Example 3: Analysis of Dissolution Rates of Mixtures Containing Crystalline Forms in Different Ratios In this example, the dissolution rates of the particles of the mixtures of the crystalline forms A and G in different ratios were examined. Specifically, 2 mg of each of the mixtures prepared in Preparative Examples 8 to 11 was filled in a hard capsule and was then eluted in 900 ml of a pH 1.2 solution at a revolution number of 100 rpm and a temperature of 37±0.5° C. for 2 hr. The eluted particles were analyzed under the same HPLC conditions as described in Test Example 1. The experimental results are shown in FIG. 10.

Figure 10:
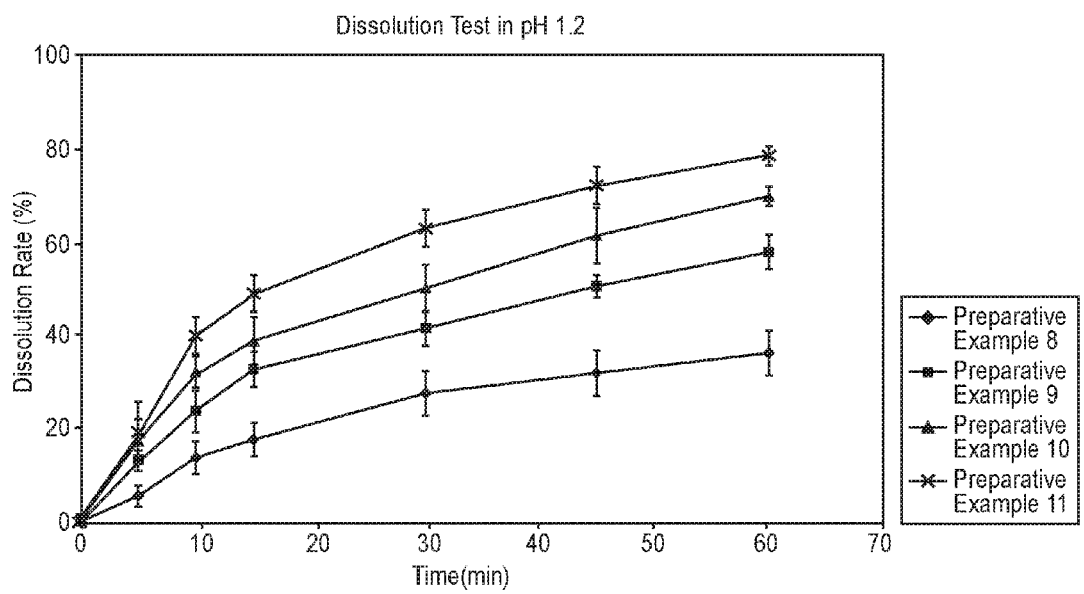
FIG. 10 is a graph showing the dissolution rates for mixtures of crystalline forms prepared in Preparative Examples 8 to 11.

As can be seen from FIG. 10, the dissolution rate increased with increasing proportion of the crystalline form A.

Test Example 4: Analysis of Pharmacokinetic Properties of Different Crystalline Forms The pharmacokinetic properties of the different crystalline forms of the compound of Formula 1 were analyzed in vivo. About 5 mg of each of the crystalline form A of Preparative Example 5 and the crystalline form G of Preparative Example 6 was suspended in 10 mL of a 0.5% methylcellulose solution to produce a formulation for oral use. Then, 6 week old male SD rats (Orient Bio. Inc., Korea) were divided into two groups. About 3 mL (10 mL/Kg) of the oral formulation was once administered orally to each rat and blood samples were drawn from the rat at predetermined intervals of 0.167, 0.5, 1.0, 2.0, 4.0, 6.0, 8.0, and 24.0 hr. The blood samples were used to analyze the pharmacokinetic parameters of the crystalline form.

The pharmacokinetic parameters of the crystalline forms were analyzed using Waters Quattro premier XE 2795 Alliance HT (Waters) under the following conditions: flow rate=0.25 ml/min, column temperature=40° C., injection volume=7 μL, and mobile phase=A: 1 mM ammonium acetate & 0.1% acetic acid (35%), B: ACN (65%). Linearity was established with 8 different standard concentrations.

The oral formulations including the compound of Preparative Example 5 and the compound of Preparative Example 6, respectively, were administered to the different rats. The blood levels of the compounds over time are graphically shown in FIG. 11. $C_{max}$(ng/mL), $T_{max}$ (hr), and AUC (hr*ng/mL) were calculated from the graph and are shown in Table 7.

TABLE 7

| Parameter | $C_{max}$ (ng/mL) | $T_{max}$ (hr) | AUC (hr * ng/mL) |
|---|---|---|---|
| Preparative Example 5 | 750.582 | 0.5 | 2317.926 |
| Preparative Example 6 | 513.614 | 1.0 | 2416.835 |

Figure 11:
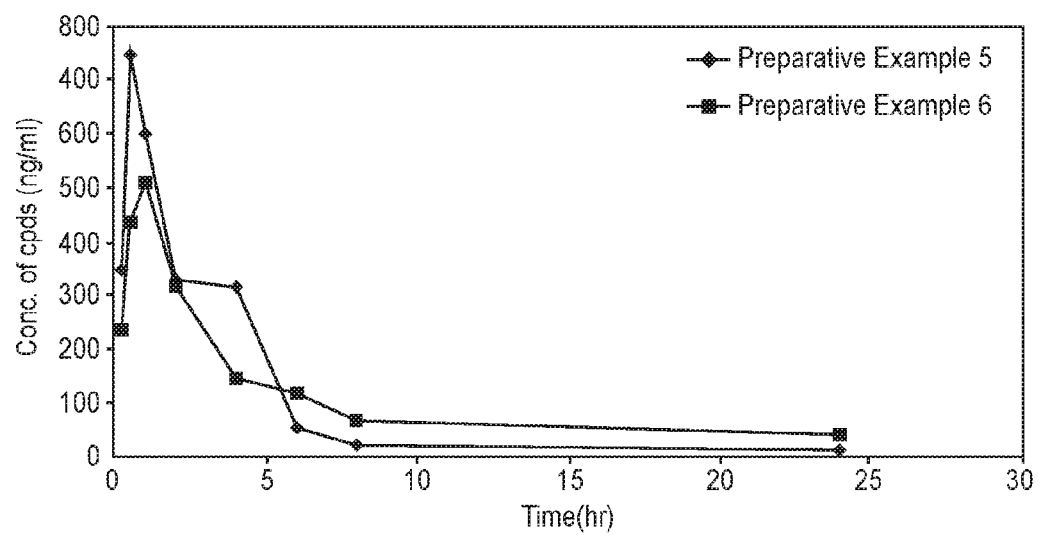
FIG. 11 is a graph showing the pharmacokinetic properties for crystalline forms prepared in Preparative Examples 5 and 6 in rats.

As shown in FIG. 11, the crystalline form A of Preparative Example 5 showed higher in vivo dissolution rates than the crystalline form G of Preparative Example 6. As can be seen from the results in Table 7, the crystalline form A of Preparative Example 5 had higher $C_{max}$ and $T_{max}$ values than the crystalline form G of Preparative Example 6, demonstrating a faster efficacy of the crystalline form A of Preparative Example 5.

Example 39 and Comparative Examples 1 and 2: Preparation of Crystalline Form with Different Particle Sizes In order to compare the characteristics of the compound of Formula 1 as a drug depending on its particle size, the crystalline form was processed into different particle diameters by the following procedures.

Comparative Example 1

The crystalline form prepared in Preparative Example 1 was called "Comparative Example 1".

Comparative Example 2

The crystalline form of Comparative Example 1 was once pulverized using a mill (Jet mill, JE POWDER) under the following conditions: screw feeder=7 rpm, agitator=7 rpm, ejector pressure=5.0 kg/cm$^2$, and line pressure=3.5 kg/cm$^2$. The pulverized crystalline form was called "Comparative Example 2".

Example 39

The crystalline form of Comparative Example 1 was once more pulverized using a mill (Jet mill, JE POWDER) under the following conditions: screw feeder=7 rpm, agitator=7 rpm, ejector pressure=5.0 kg/cm$^2$, and line pressure=3.5 kg/cm$^2$. The fine crystalline form was called "Example 39".

Test Example 5: Analysis of Particle Sizes and Measurement of Dissolution Rates of Crystalline Form with Different Particle Sizes <5-1> Analysis of the Particle Sizes The particle sizes of the crystalline form of Comparative Examples 1 and 2 and Example 39 were analyzed using a laser diffraction-based particle size analyzer (Mastersizer 2000®, Malvern). After each sample was fed into a dry module (Scirocco 2000®, Malvern) at a pressure of 2 bar, the 50% volume particle diameter ($d_{(0.5)}$) and 90% volume particle diameter ($d_{(0.9)}$) of the particles were measured. The experimental results are shown in Table 8.

TABLE 8

|  | Particle size (μm) | | |
| --- | --- | --- | --- |
|  | $d_{(0.1)}$ | $d_{(0.5)}$ | $d_{(0.9)}$ |
| Comparative Example 1 | 40.55 | 136.49 | 527.04 |
| Comparative Example 2 | 5.15 | 32.17 | 83.54 |
| Example 39 | 1.75 | 5.98 | 15.23 |

As can be seen from the results in Table 8, the particles of Comparative Example 1 had a 50% volume particle diameter ($d_{(0.5)}$) of 136.49 μm and a 90% volume particle diameter ($d_{(0.9)}$) of 527.04 m, the particles of Comparative Example 2 had a 50% volume particle diameter ($d_{(0.5)}$) of 32.17 μm and a 90% volume particle diameter ($d_{(0.9)}$) of 83.54 μm, and the particles of Example 39 had a 50% volume particle diameter ($d_{(0.5)}$) of 5.98 μm and a 90% volume particle diameter ($d_{(0.9)}$) of 15.23 μm. From these results, it could be confirmed that the crystalline forms of Comparative Examples 1 and 2 and Example 39 had different particle size distributions.

<5-2> Analysis of Dissolution Rates of Crystalline Form with Different Particle Sizes In this example, the dissolution rates of the crystalline form with different particle sizes were examined. The particles of Comparative Examples 1 and 2 and Example 39 were filled in different hard capsules (2 mg per capsule) and were then eluted in 900 ml of a pH 1.2 solution and 900 ml of a pH 6.8 solution at a revolution number of 100 rpm and a temperature of 37±0.5° C. for 3 hr. The eluted particles were analyzed under the same HPLC conditions as described in Test Example 1.

The results are shown in FIGS. 12a and 12b.

As can be seen from FIGS. 12a and 12b, the particles of Example 39_having a 50% volume particle diameter ($d_{(0.5)}$) of 3 μm to 9 μm and a 90% volume particle diameter ($d_{(0.9)}$) of 10 μm to 50 μm showed higher dissolution rates than the particles of Comparative Examples 1 and 2 whose 50% volume particle diameters and 90% volume particle diameters were outside the particle size distribution ranges of the particles of Example 39. These results show that a higher dissolution rate can be attained when the 50% volume particle diameter ($d_{(0.5)}$) and the 90% volume particle diameter ($d_{(0.5)}$) of the crystalline form A of the compound of Formula 1 are adjusted to the ranges of 3 μm to 9 μm and 10 μm to 50 μm, respectively.

Test Example 6: Analysis of Stability of Crystalline Form of Compound of Formula 1

<6-1> Temperature Stability

The crystalline form A of Example 39 was filled in hard capsules (2 mg per capsule), packaged with PTP, and stored for 72 hr under the severe temperature conditions shown in Table 9. During the storage, the appearance of the crystalline form A, the retention time of the major peak, the amounts (%) of related substances, and the compound content were observed. The retention time of the major peak, the amounts of related substances, and the compound content were analyzed by HPLC under the following conditions. The results are shown in Table 9.

<HPLC Conditions for Analysis of Related Substances>

Column: Hypurity C18, 250×4.6 mm, 5 m or its equivalent column

Detector: UV absorption spectrometer (measured at 241 nm)

Injection volume: 20 μl

Flow rate: 1.0 ml/min

Column temperature: 30° C.

Mobile phase: A—acetonitrile, B—0.1% v/v trifluoroacetic acid (TFA) in water

| Time (min) | Flow rate (mL/min) | A (%) | B (%) |
| --- | --- | --- | --- |
| 0.00 | 1.0 | 38 | 62 |
| 30.00 | 1.0 | 38 | 62 |
| 35.00 | 1.0 | 90 | 10 |
| 45.00 | 1.0 | 90 | 10 |
| 45.01 | 1.0 | 38 | 62 |
| 50.00 | 1.0 | 38 | 62 |

<HPLC Conditions for Analysis of the Compound Content>

Column: Hypurity C18, 250×4.6 mm, 5 m or its equivalent column

Detector: UV absorption spectrometer (measured at 325 nm)

Injection volume: 20 μl

Flow rate: 1.5 ml/min

Column temperature: 30° C.

Mobile phase: A—acetonitrile, B—water, A:B=60:40, v/v %

Analysis time: 5 min

Diluent: water:acetonitrile=50:50, v/v %

TABLE 9

| Test item | Criteria | Packaging material PTP Stability test conditions (severe temperature conditions) | | | |
|---|---|---|---|---|---|
| | | 60 ± 2° C. 60 ± 5% RH 24 hr | 80 ± 2° C. 60 ± 5% RH 24 hr | 90 ± 2° C. 60 ± 5% RH 24 hr | 90 ± 2° C. 60 ± 5% RH 72 hr |
| | | Results | | | |
| Appearance | White hard capsule containing white-pale yellow powder and marked with upper green CG649 | Unchanged | Unchanged | Unchanged | Unchanged |
| Peak retention time confirmation | Retention time (RT) of major peak (HPLC) | The same RT | The same RT | The same RT | The same RT |
| Amounts of related substances | Each <0.3%, Total <1.0% | 0.0%, 0.0% | 0.0%, 0.0% | 0.0%, 0.0% | 0.1%, 0.1% |
| Content | 95-105% | 103.0% | 101.5% | 101.8% | 101.1% |

As can be seen from the results in Table 9, the appearance of the crystalline form A remained unchanged, and no significant decrease in the content of the crystalline form A and no significant increase in the amount of related substances were observed under severe temperature conditions. These results demonstrate high stability of the crystalline form A under the temperature conditions.

<6-2> Humidity Stability

The crystalline form A of Example 39 was evaluated for humidity stability in the same manner as in Test Example <6-1>. The crystalline form A was filled in a hard capsule (2 mg per capsule) and stored under the severe humidity conditions shown in Table 10. Thereafter, the appearance of the crystalline form A, the retention time of the major peak, the amounts (%) of related substances, and the compound content were analyzed. The results are shown in Table 10.

TABLE 10

| Test item | Criteria | Packaging material PTP Stability test conditions (severe humidity conditions) | | |
|---|---|---|---|---|
| | | 25 ± 2° C. 90 ± 5% RH 1 week | 25 ± 2° C. 90 ± 5% RH 2 weeks | 25 ± 2° C. 90 ± 5% RH 4 weeks |
| | | Results | | |
| Appearance | White hard capsule containing white-pale yellow powder and marked with upper green CG649 | Unchanged | Unchanged | Unchanged |
| Peak retention time confirmation | Retention time (RT) of major peak (HPLC) | The same RT | The same RT | The same RT |
| Amounts of related substances | Each <0.3%, Total <1.0% | 0.1% 0.1%, | 0.1%, 0.1% | 0.1%, 0.1% |
| Content | 95-105% | 103.1% | 103.1% | 101.2% |

As can be seen from the results in Table 10, the appearance of the crystalline form A remained unchanged, and no significant decrease in the content of the crystalline form A and no significant increase in the amount of related substances were observed under severe humidity conditions. These results demonstrate high stability of the crystalline form A under the humidity conditions.

<6-3> Light Stability

The crystalline form A of Example 39 was evaluated for light stability in the same manner as in Test Example <6-1>. The crystalline form A was filled in a hard capsule (2 mg per capsule) and stored under the light stress conditions shown in Table 11. Thereafter, the appearance of the crystalline form A, the retention time of the major peak, the amounts (%) of related substances, and the compound content were analyzed. The results are shown in Table 11 and FIG. 13.

TABLE 11

| Test item | Criteria | Packaging material PTP Stability test conditions (light stress conditions) | | |
|---|---|---|---|---|
| | | Light* 1 week | Light* 2 weeks Results | Light* 4 weeks |
| Appearance | White hard capsule containing white-pale yellow powder and marked with upper green CG649 | Unchanged | Unchanged | Unchanged |
| Peak retention time confirmation | Retention time (RT) of major peak (HPLC) | The same RT | The same RT | The same RT |
| Amounts of related substances | Each <0.3%, Total <1.0% | 1.7%, 3.0% | 2.1%, 3.7% | 2.3%, 4.1% |
| Content | 95-105% | 103.4% | 103.1% | 99.1% |

Figure 13:
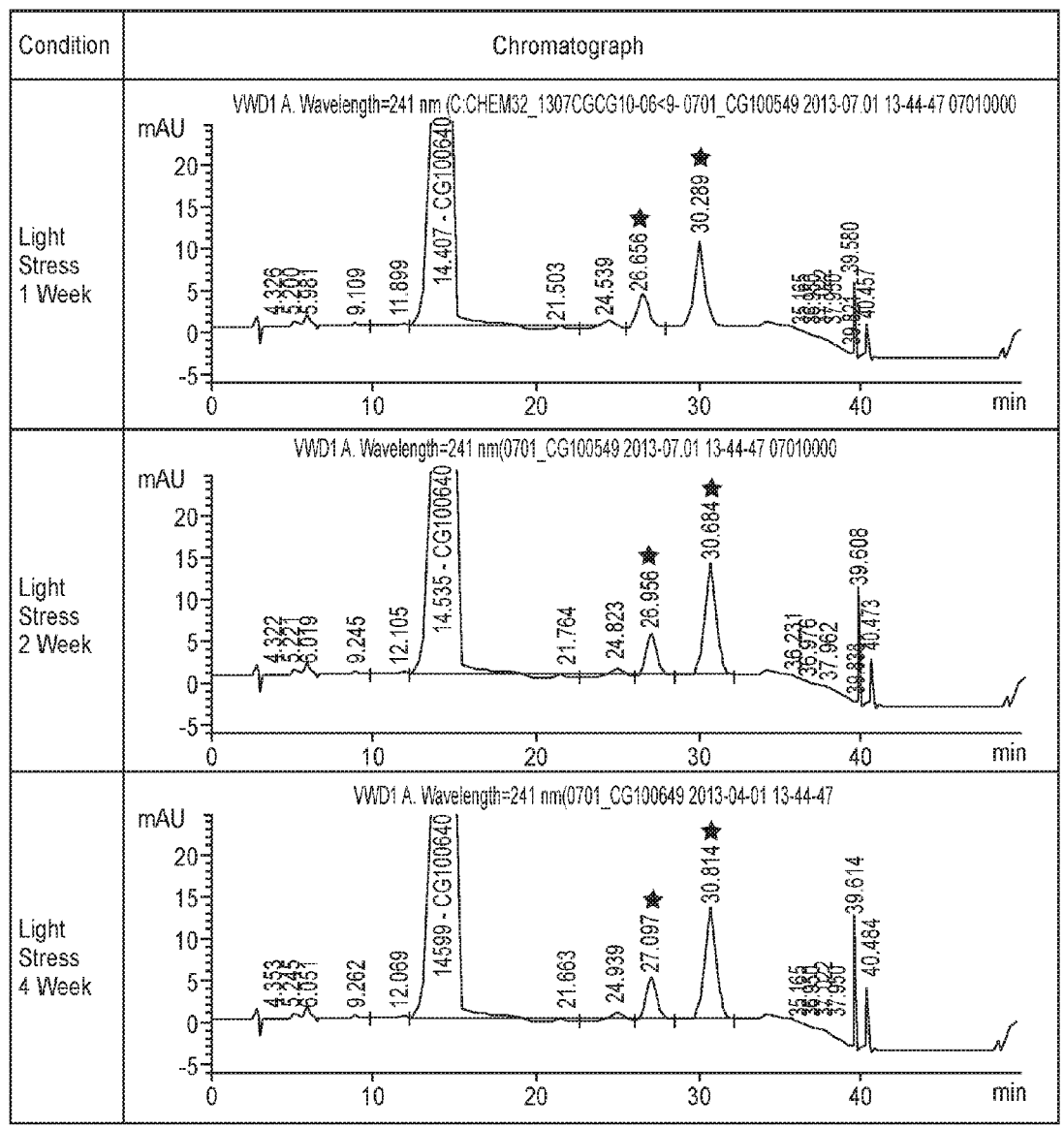
FIG. 13 shows chromatograms of formulations including a crystalline form of Example 39, as analyzed by HPLC after storage under light stress conditions; peaks marked with ★ indicate that related substances created under the light stress conditions exceeded the respective reference standards defined by related substance test methods.

*indicates the time when irradiated with light from a white florescent lamp and a UV florescent lamp up to a total illumination of $1.2 \times 10^6$ lux · hr, 200 W · hr/m$^2$ As can be seen from Table 11 and FIG. 13, the crystalline form A produced related substances exceeding the criteria within 7 days under light stress storage conditions. These results lead to the conclusion that the raw materials should be stored and the formulations should be stored and produced in the dark or in environments protected from exposure to strong light. Light shielding conditions are required in actual processes.

Examples 40 to 49: Productions of Capsule Formulations Including Crystalline Form of Present Invention In order to find optimum pharmaceutical additives suitable for the crystalline form A, the diluents and lubricants shown in Tables 12 and 13 were used to produce capsule formulations.

The Carr's index of each capsule formulation was measured by the Carr's method using a tapped density tester (Erweka, SVM 101) and the angle of repose of each capsule formulation was determined by the fixed funnel method such as the dropping method.

TABLE 12

| | | Example 40 | Example 41 | Example 42 | Example 43 | Example 44 |
|---|---|---|---|---|---|---|
| Active ingredient | Crystalline form A of the compound of Formula 1 | 1 | 1 | 1 | 1 | 1 |
| Diluents | Silicified microcrystalline cellulose 50 (Prosolv SMCC 50) | 98 | — | — | — | — |
| | Silicified microcrystalline cellulose 90 (Prosolv SMCC 90) | — | 98 | — | — | — |
| | Microcrystalline cellulose (MCC) | — | — | 98 | — | — |
| | Lactose (Flow lac 100) | — | — | — | 98 | — |
| | Cellactose 80 | — | — | — | — | 98 |
| Lubricants | Talc | 1 | 1 | 1 | 1 | 1 |
| | Stearic acid | — | — | — | — | — |
| | Total | 100 | 100 | 100 | 100 | 100 |
| | Carr's index | 29.8 | 22.1 | 33.3 | 14.6 | 24.2 |
| | Angle of Repose | 34.6 | 30.2 | 40.3 | 31.5 | 33.3 |

TABLE 13

|  |  | Example 45 | Example 46 | Example 47 | Example 48 | Example 49 |
|---|---|---|---|---|---|---|
| Active ingredient | Crystalline form A of the compound of Formula 1 | 1 | 1 | 1 | 1 | 1 |
| Diluents | Silicified microcrystalline cellulose 50 (Prosolv SMCC 50) | 98 | — | — | — | — |
|  | Silicified microcrystalline cellulose 90 (Prosolv SMCC 90) | — | 98 | — | — | — |
|  | Microcrystalline cellulose (MCC) | — | — | 98 | — | — |
|  | Lactose (Flow lac 100) | — | — | — | 98 | — |
|  | Cellactose 80 | — | — | — | — | 98 |
| Lubricants | Talc | — | — | — | — | — |
|  | Stearic acid | 1 | 1 | 1 | 1 | 1 |
|  | Total | 100 | 100 | 100 | 100 | 100 |
|  | Carr's index | 29.9 | 21.9 | 32.8 | 14.6 | 24.1 |
|  | Angle of Repose | 34.5 | 32.3 | 37.2 | 31.5 | 33.6 |

As can be seen from the results in Tables 12 and 13, the capsule formulations containing silicified microcrystalline cellulose 50, silicified microcrystalline cellulose 90, microcrystalline cellulose, lactose or Cellactose 80 as a diluent and talc or stearic acid as a lubricant (Example 40 to 49) had angles of repose in the range of 30° to 400 and a Carr's index in the range of 21% to 30%. Within these ranges, good flowability of the powders is ensured, thus being suitable for capsule filling. However, the capsule formulations of Examples 45 to 49 using stearic acid as a lubricant had considerably high water contents despite the same experimental conditions as in Examples 40 to 44. Therefore, it can be concluded that the capsule formulations of Examples 45 to 49 are difficult to produce in a highly humid environment or season, and therefore, the use of talc as a lubricant would be more desirable.

Test Example 7: Measurement of Particle Size Distributions

The particle size distributions of the formulations produced in Examples 40 to 44 were measured using 40-, 60-, 70-, 80-, 120-, 140-, 200-, and 270-mesh standard sieves in accordance with the sieve classification method (method II) described in the standard test methods for particle size of the Korean Pharmacopoeia. The results are shown in FIG. 14.

Figure 14:
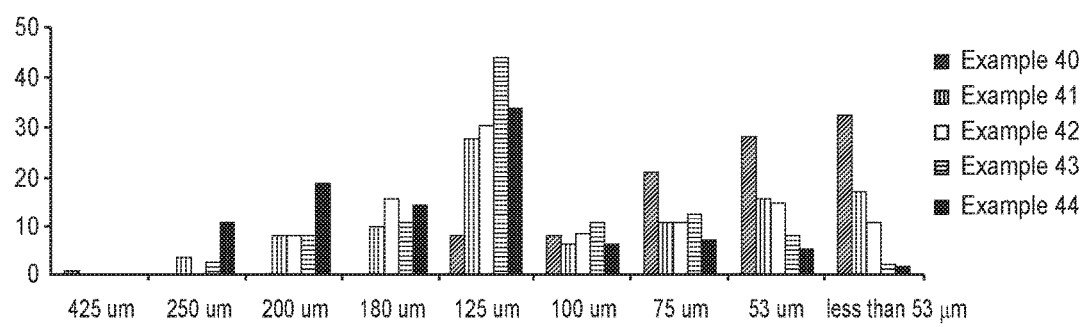
FIG. 14 is a graph showing the particle size distributions of formulations produced in Examples 40 to 44.

As shown in FIG. 14, the particle size distributions varied greatly depending on the kind of the diluent and the lubricant used.

Particularly, the formulation of Example 40 produced using silicified microcrystalline cellulose 50 as a diluent showed a uniform particle size distribution in the particle diameter range of less than 125 μm, indicating high mixing uniformity. Silicified microcrystalline cellulose 50 would be more suitable for use in the composition of the present invention due to its high flowability, improved lubricating effects, and ease of mixing compared to other diluents.

Test Example 8: Analysis of Formulation Uniformity

The capsule formulations produced in Examples 40 to 44 were tested for uniformity in accordance with the test method for content uniformity described in the standard test methods for formulation uniformity of the Korean Pharmacopoeia. Six samples were taken from each capsule formulation. The contents of the major ingredient in the samples were measured to determine the average content, standard deviation, and assessed value (AV). The experimental results are shown in Table 14.

TABLE 14

|  | Average content (%) | Standard deviation | Assessed value (AV) |
|---|---|---|---|
| Example 40 | 99.2 | 1.2 | 2.8 |
| Example 41 | 92.9 | 4.9 | 9.2 |
| Example 42 | 99.1 | 2.2 | 5.3 |
| Example 43 | 90.9 | 5.2 | 12.1 |
| Example 44 | 101.1 | 2.0 | 4.7 |

As can be seen from the results in Table 14, the formulations were found to have good uniformity. Particularly, the formulation of Example 40 had the lowest assessed value (AV), indicating the best uniformity.

Example 45: Productions of Oral Tablet Formulation Including Crystalline Form of Present Invention A tablet as an oral pharmacological formulation was manufactured by using the raw material of the compound of Formula 1 having the crystalline form A as mentioned above. Table 15 shows composition of an oral pharmacological tablet formulation. The method for manufacturing is as follows. The major ingredient and the excipient were triturated and mixed 2 to 4 times and subjected to dry granulation in a povidone aqueous solution to primarily manufacture a mixture. Then, the excipient and the lubricant were added thereto in order and tableted. The resulting tablet was coated to obtain a final product. The produced tablet was subjected to a stability test under accelerated conditions (40±2° C./75±5% RH). The results are shown in Table 16. As can be seen from the Table, content, formulation uniformity, dissolution and related substances were maintained constantly within a range of the reference standard during 6 month acceleration. Thus, it can be said that stability of the formulation is secured.

TABLE 15

Composition of manufactured oral pharmaceutical tablet formulation

| Function | Ingredient | Standard | % W/W |
|---|---|---|---|
| Major ingredient | Polmacoxib | Annexed Standard | 1.9 |
| Disintegrating agent | Sodium starch glycolate | NF | 6.8 |
| Excipient | Silicified microcrystalline cellulose | NF | 84.5 |
| Lubricant | Magnesium stearate | KP | 1.0 |
| Binding agent | Povidone | JP | 2.9 |
| Coating agent | Opadry blue | Annexed Standard | Suitable amount. |
| Total | | | 100% |

TABLE 16

Results of stability test for tablet under accelerated test conditions

| Test item | Test criteria | Initiation | 3 month | 6 month |
|---|---|---|---|---|
| Dissolution | 30 min, 75% or more | Min 88% | Min 90% | Min 88% |
| Related substance | Each related substance < 0.3% | Not detected | Not detected | Max 0.05% |
| | Total related substance < 1.0% | Not detected | Not detected | 0.06% |
| Formulation Uniformity | Assessed value within 15.0% | 2.4% | — | 2.5% |
| Content | 95.0~105.0% | 100.7% | 101.0% | 102.7% |

What is claimed is:

1. An anti-inflammatory pharmaceutical composition comprising the compound of Formula 1 or a pharmaceutically acceptable salt thereof having crystalline form A, crystalline form G or a mixture thereof having the respective results of X-ray diffraction analysis shown in Tables 4 (crystalline form A) and 5 (crystalline form G) and the results of differential scanning calorimetry (DSC) analysis illustrated in FIGS. 3 (crystalline form A) and 4 (crystalline form G).

2. The anti-inflammatory pharmaceutical composition according to claim 1, wherein the compound of Formula 1 or a pharmaceutically acceptable salt thereof has a 50% volume particle diameter ($d_{(0.5)}$) of 3 μm to 9 μm and a 90% volume particle diameter ($d_{(0.9)}$) of 10 μm to 50 μm.

3. The anti-inflammatory pharmaceutical composition according to claim 1 or claim 2, which further comprises (ii) a pharmaceutically acceptable diluent; and (iii) a pharmaceutically acceptable lubricant.

4. The anti-inflammatory pharmaceutical composition according to claim 3, wherein the compound of Formula 1 or a pharmaceutically acceptable salt thereof comprises at least 50% by weight of the crystalline form A.

5. The anti-inflammatory pharmaceutical composition according to claim 3, wherein the diluent is any one selected from the group consisting of silicified microcrystalline cellulose, microcrystalline cellulose, cellulose, lactose, and combinations thereof.

6. The anti-inflammatory pharmaceutical composition according to claim 3, wherein the lubricant is talc or stearic acid.

7. The anti-inflammatory pharmaceutical composition according to claim 3, wherein the pharmaceutical composition comprises 0.5% to 20% by weight of the compound of Formula 1 or a pharmaceutically acceptable salt thereof, 75% to 99% by weight of the diluent, and 0.1% to 5% by weight of the lubricant.

8. The anti-inflammatory pharmaceutical composition according to claim 3, wherein the pharmaceutical composition comprises 1% to 2% by weight of the compound of Formula 1 or a pharmaceutically acceptable salt thereof, 98% to 99% by weight of the diluent, and 1% by weight of the lubricant.

9. A formulation comprising the pharmaceutical composition according to claim 3 in a capsule form or a tablet form.

* * * * *